US009201058B2

(12) United States Patent
Hibbs et al.

(10) Patent No.: US 9,201,058 B2
(45) Date of Patent: Dec. 1, 2015

(54) APPARATUS AND METHOD FOR SENSING A TIME VARYING IONIC CURRENT IN AN ELECTROLYTIC SYSTEM

(75) Inventors: Andrew D. Hibbs, La Jolla, CA (US); Melissa Ann Poquette, Brea, CA (US)

(73) Assignee: Electronic Biosciences, Inc., San Diego, CA (US)

( * ) Notice: Subject to any disclaimer, the term of this patent is extended or adjusted under 35 U.S.C. 154(b) by 1392 days.

(21) Appl. No.: 12/304,543

(22) PCT Filed: May 10, 2007

(86) PCT No.: PCT/US2007/011257
§ 371 (c)(1),
(2), (4) Date: Dec. 12, 2008

(87) PCT Pub. No.: WO2007/145748
PCT Pub. Date: Dec. 21, 2007

(65) Prior Publication Data
US 2009/0194429 A1    Aug. 6, 2009

Related U.S. Application Data

(60) Provisional application No. 60/813,712, filed on Jun. 15, 2006.

(51) Int. Cl.
*G01N 33/487*    (2006.01)

(52) U.S. Cl.
CPC .... *G01N 33/48728* (2013.01); *G01N 33/48721* (2013.01)

(58) Field of Classification Search
CPC ................... G01N 33/47821; G01N 33/48728
USPC .................................................. 204/403.06
See application file for complete search history.

(56) References Cited

U.S. PATENT DOCUMENTS 4,909,919 A    3/1990  Morris et al.
6,627,067 B1 *    9/2003  Branton et al. ............... 205/778
(Continued)

FOREIGN PATENT DOCUMENTS

WO    WO 02103354 A1 *    12/2002
WO    2006/012571    2/2006
(Continued)

OTHER PUBLICATIONS

Applied Nanostructures, http://www.appnano.com/, Accessed Apr. 4, 2007.
(Continued)

*Primary Examiner* — Luan Van
*Assistant Examiner* — Louis Rufo
(74) *Attorney, Agent, or Firm* — Diederiks & Whitelaw, PLC (57) ABSTRACT

An apparatus and method for sensing time varying ionic current in an electrolytic system having a first fluid chamber and a second fluid chamber separated by a barrier structure is provided, wherein the barrier structure includes thick walls and a substrate having an orifice therein, with the first and second fluid chambers being in communication via the orifice. A potential is applied between electrodes in respective first and second fluid chambers, thus driving an electrical current between them and through the orifice. Total capacitance of the system is less than 10 pF. Analytes are added to one of the first and second fluid chambers and time varying ionic current that passes across the orifice is measured. An amplifier proximal to the barrier structure and electrodes amplifies the ionic current signal.

24 Claims, 6 Drawing Sheets

(56) References Cited

U.S. PATENT DOCUMENTS

| | | |
|---|---|---|
| 6,961,601 B2 | 11/2005 | Matthews et al. |
| 2008/0121534 A1 | 5/2008 | White et al. |
| 2008/0218184 A1 | 9/2008 | White et al. |

FOREIGN PATENT DOCUMENTS

| | | | |
|---|---|---|---|
| WO | WO 2006012571 A1 | * | 2/2006 |
| WO | 2007/001410 | | 1/2007 |

OTHER PUBLICATIONS

Axon Instruments, Inc., "The Axon Guide for Electrophysiology & Biophysics Laboratory Techniques", Part No. 2500-102 Rev A.

Bard et al., "Electrochemical Methods: Fundamentals and Applications", John Wiley & Sons, Inc., pp. 632-658, 2001.

Beckman Coulter, The Coulter Counter, Multisizer 3 Coulter Counter, www.beckmancoulter.com.

Ames, SmithKline Beecham Pharmaceuticals, "FLIPR: a Platform for Orphan G-protein Coupled Receptor Functional Genomics", SBS Congress, 2000.

Connolly et al., "Drugs Active at T-Type $Ca^{2+}$ Channels", Voltage-Gated Ion Channels as Drug Targets, Wiley-VCH Verlag GmbH & Co. KGaA, pp. 84-99, 2006.

Cremer et al., "Formation and Spreading of Lipid Bilayers on Planar Glass Supports", American Chemical Society, No. 103, pp. 2554-2559, 1999.

Doering et al., "Overview of Voltage-Gated Calcium Channels", Wiley-VCH Verlag GmbH & Co. KGaA, pp. 65-83, 2006.

Gu et al., "Stochastic Sensing of Organic Analytes by a Pore-Forming Protein Containing a Molecular Adapter", Nature, vol. 398, pp. 686-690, 1999.

Haydon et al., "Ion Transport Across Thin Lipid Membranes: a Critical Discussion of Mechanisms in Selected Systems", Quarterly Review of Biophysics, vol. 5, pp. 187-282, 1972.

Hille, "Ion Channels of Excitable Membranes", Sinauer Associates, Inc., pp. 393-403, 2001.

Hladky, "Ion Currents Through Pores: The Roles of Diffusion and External Access Steps in Determining the Currents through Narrow Pores", Biophysical Journal, vol. 46, pp. 293-297, 1984.

Hladky et al., "Ion Transfer Across Lipid Membranes in the Presence of Gramicidin A", Biochim. Biophys. Acta., No. 274, pp. 294-312, 1972.

Hodgkin et al., "Currents Carried by Sodium and Potassium Ions Through the Membrane of the Giant Axon of Loligo", J. Physiol., No. 116, pp. 449-472, 1952.

Hodgkin et al., "A Quantitative Description of Membrane Current and its Application to Conduction and Excitation in Nerve", Journal of Physiology, vol. 117, pp. 500-544, 1952.

Levis et al., "Constructing a Patch Clamp Setup", Methods of Enzymology, vol. 207, pp. 14-66, 1992.

Levis et al., "Technology of Patch-Clamp Electrodes", Neuromethods, vol. 26, pp. 1-36, 1995.

Li et al., "Conical Nanpore Membranes. Preparation and Transport Properties", Analytical Chemistry, vol. 76, No. 7, pp. 2025-2030, 2004.

Mao et al., "A Microfluidic Device with a Linear Temperature Gradient for Parallel and Combinatorial Measurements", J. Am. Chem. Soc., vol. 124, pp. 4432-4435, 2002.

Marty et al., "Tight-Seal Whole-Cell Recording", Single-Channel Recording, Plenum Press, pp. 107-122, 1983.

Naumann et al., "Proton Transport through a Peptide-Tethered Bilayer Lipid Membrane by the $H^+$—ATP Synthase from Chloroplasts Measured by Impedance Spectroscopy", Biosensors & Bioelectronics, vol. 17, pp. 25-34, 2002.

PatchXpress 7000A, Molecular Devices, http://www.moleculardevices.com/pages/instruments/patchxpress.html.

Raguse et al., "Tethered Lipid Bilayer Membranes: Formation and Ionic Reservoir Characterization", Langmuir, vol. 14, pp. 648-659, 1998.

Schmidt et al., "A Chip-Based Biosensor for the Functional Analysis of Single Ion Channels", Angew. Chem. Int. Ed., vol. 39, No. 17, pp. 3137-3140, 2000.

Sigworth, "Electronic Design of the Patch Clamp", Single-Channel Recording, Plenum Press, pp. 95-127, 1995.

Sigworth, "The Patch Clamp is More Useful than Anyone Had Expected", Federation Proceedings, vol. 45, No. 12, pp. 2673-2677, 1986.

Sophion Bioscience, "Qpatch HT—Enabling New Screening Paradigms in Ion Channel Drug Discovery", http://www.sophion.dk.

Tang et al., "Perfusing Pipettes", European Journal of Physiology, vol. 416, pp. 347-350, 1990.

Wang et al., "Electrostatic-Gated Transport in Chemically Modified Glass Nanopore Electrodes", J. Am. Chem. Soc., vol. 128, pp. 7679-7686, 2006.

Watkins et al., "Zeptomole Voltammetric Detection and Electron-Transfer Rate Measurements Using Platinum Electrodes of Nanometer Dimensions", Analytical Chemistry, vol. 75, No. 16, pp. 3962-3971, 2003.

Zhang et al., "The Nanopore Electrode", Analytical Chemistry, vol. 76, No. 21, pp. 6229-6238, 2004.

Montal et al., "Formation of Bimolecular Membranes from Lipid Monolayers and a Study of Their Electrical Properties", Proc. Nat. Acad. Sci., vol. 69, No. 12, pp. 3561-3566, 1972.

* cited by examiner

APPARATUS AND METHOD FOR SENSING A TIME VARYING IONIC CURRENT IN AN ELECTROLYTIC SYSTEM

CROSS-REFERENCE TO RELATED APPLICATION

The present application represents a National Stage application of PCT/US2007/011257 filed May 10, 2007 entitled "Apparatus and Method for Sensing a Time Varying Ionic Current in an Electrolytic System", and claims the benefit of U.S. Provisional Patent Application Ser. No. 60/813,712 filed Jun. 15, 2006 entitled "System for Improved Ion Channel Recordings and Related Measurement of Objects and Analytes in Solution."

BACKGROUND OF THE INVENTION

1. Field of the Invention

The present invention pertains to the art of electrolytic sensing systems, and more specifically, to an apparatus and method for sensing a time varying ionic current in an electrolytic environment having improved sensitivity and bandwidth.

2. Discussion of the Prior Art

The measurement of the electrical conductivity of small fluid regions is of importance in many applications. For example, small particles, such as viruses, suspended in a fluid can be counted using a resistive pulse technique, i.e. measuring the momentary change they produce in the average fluid conductance as they pass through an orifice. In recent years, it has become of great scientific and technological importance to measure the variation in electrical conductivity of entities that span the membrane wall of a cell. Such entities, which include protein pores, ion channels, transporters, and related entities (herein denoted by the group name: ion channels), control the passage of specific ions into and/or out of a cell. Measuring the ion fluxes by the electrical current they carry is much easier, faster, and more fundamental than by other methods such as a radioactive tracer.

Electrical measurements of ion channel activity go back to Hodgkin and Huxley's identification of currents flowing through homogeneous ensembles of channels that they called "ionic conductances". Measurements of currents through single channel proteins, one molecule at a time, began with the work of Haydon and Hladky. They found that currents through single gramicidin channels had a rectangular time course, and that the duration of opening corresponded to the time-dependent processes studied by Hodgkin and Huxley, while the amplitude of the current through the channel corresponded to the "instantaneous current" recorded by them.

Hundreds of types of ion channels have been investigated to date with electrical methods, leaving thousands of ion channels and transporters yet to study. Channel currents vary from the currently unmeasurable (~0.2 Pico Amps (pA)) to hundreds of pA. Indeed, many of the biologically and medically important ion channels have unmeasurable single channel currents, and their conductance must be estimated from macroscopic measurements of many ion channels. In addition to a need to be able to record smaller current changes, it is generally believed that the speed of many ion channel transitions is faster than the response time of existing recording systems and thus these channels have gone unmeasured.

Figure 1:
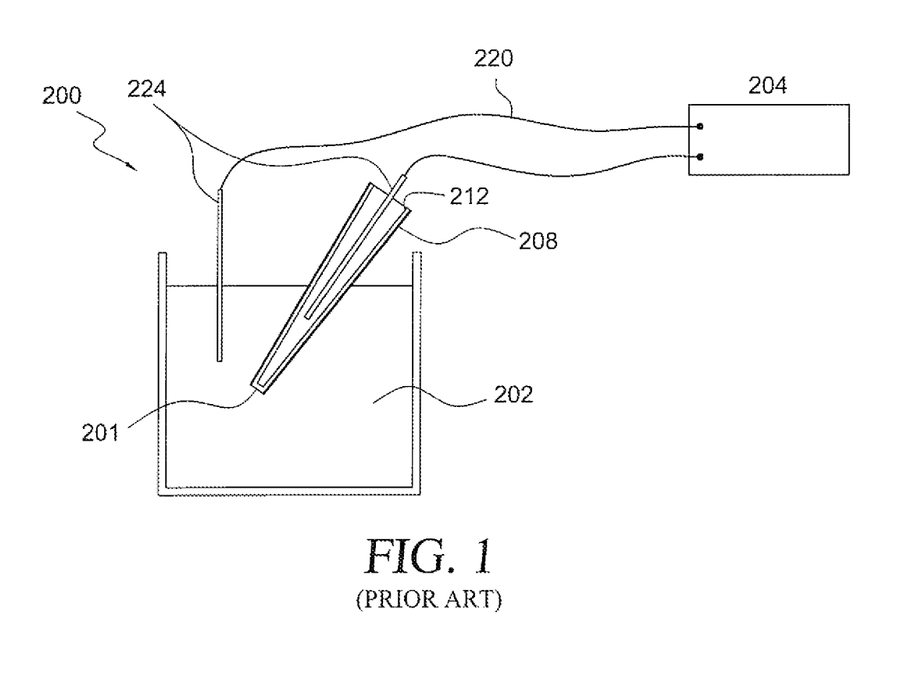
FIG. 1 depicts a conventional prior art patch clamp sensing system.

The principal advance in recording ion channels was made by Sakmann and Neher who developed a patch pipette method that allowed recording of single channel currents with a thin-walled, drawn-glass pipette pressed against a cell membrane. One example of such a system is depicted in FIG. 1. Although not shown, the entire patch clamp apparatus would typically be enclosed in an electrically conducting shield to minimize the pick-up of electromagnetic noise. It was found that the measurement fidelity could be increased significantly by drawing the membrane several microns into the pipette by suction so as to increase the area of the membrane in contact with the surface of the glass. The norm is for the pipette to be positioned by hand. In automated cell patching systems, cells are drawn by suction to a micron-scale orifice in a glass or silicon surface. Regardless, once the cell is attached, an electrical circuit across an ion channel must be completed by penetrating the cell membrane with a sharp electrode or tearing off a patch of cell membrane attached to the measurement region to allow the part of the ion channel on the inside surface of the cell to be exposed to the electrolyte in the bath.

Figure 2:
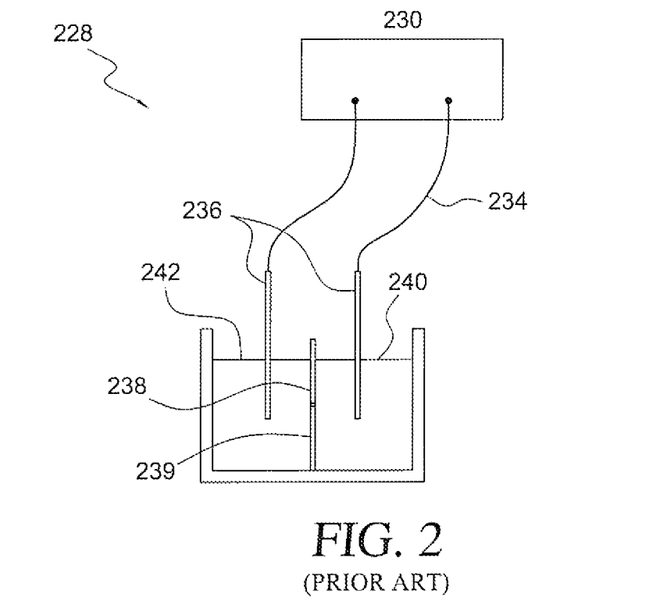
FIG. 2 depicts a conventional prior art artificial membrane sensing system.

An alternate, more direct, route is to create a membrane incorporating an ion channel and either suspend the membrane over an orifice (typically in the order of 100 microns or micrometers (μm) in diameter) in a solid material such as Teflon, or support it with a solid electrode surface, possibly via polymer tethers. One example of such a suspended artificial membrane system is depicted in FIG. 2. Although not shown, this system would typically be enclosed by an electrically conducting shield. The former method permits macroscopic access from both sides of the membrane, but is very fragile. The latter is robust, but the chemistry of the lipid and polymer tethers requires that an inert electrode (e.g. gold) that has a predominantly capacitive (i.e. alternating current (AC)) coupling to the electrolyte must be used. In addition, the very small fluid volume in the region between the membrane and solid surface prevents the use of traditional direct current (DC) methods to measure channel current because of the build up of ionic concentration gradients across the membrane.

Regarding measurement sensitivity and bandwidth, conventional ion channel recordings are limited by the current noise of the first stage amplifier, and the effective current noise produced by the voltage noise of the first stage amplifier acting on the total capacitance at the amplifier input.

Referring to FIG. 1, a typical patch clamp system 200 including a membrane 201 and an electrolyte bath 202 has the following properties. The input capacitance of a first stage amplifier 204 is 15 picofarads (pF). The capacitance of a pipette holder 208 varies from 1-5 pF, and the capacitance of a pipette 212 is 1-5 pF also. Larger pipette capacitances are associated with holders that have metallic shielding (Axon Instruments). However, the immersion of the thin walled tip of the patch pipette into the bath 202 produces a further capacitance in the order of 1 pF/mm. Although it is possible to immerse a pipette tip by only a very small distance, it is cumbersome to set up, and difficult to implement for any length of time because of the fluid level change due to evaporation. For a typical tip immersion distance of 5 millimeters (mm), the extra capacitance is 5 pF, and is a fundamental result of the pipette tip having a very thin wall. The capacitance of a wire 220 running from an electrode 224 to the system electronics depends on the wire diameter and length. Assuming the wire is 1 mm in diameter and 20 centimeters (cm) long, and the shield (not shown) is from 10 cm to 1 meter (cm) away, the wire capacitance is 1.5-2.1 pF. Taken together, the total capacitance at the amplifier input is the range of 25-30 pF.

The capacitance of the artificial membrane apparatus 228 is typically higher. Referring to FIG. 2, the same capacitance values are found for a first stage amplifier 230 and connecting wires 234 that connect first stage amplifier 230 to electrodes 236, but a membrane 238 suspended on a Teflon sheet 239 that divides two fluid volumes 240 and 242 has an area 1,000-10,000 times larger than membrane 201 of the patch pipette system. This produces an additional shunt capacitance in the range of 5-100 pF. In addition, the capacitance of the measurement side of the electrolyte bath or fluid volume 240 produces a capacitance that scales linearly with the bath radius and is typically at least 1 pF. Overall, the total capacitance at the amplifier input of the prior art artificial membrane apparatus is 22-120 pF.

The above prior art systems are well optimized in the sense that the internal contributions to the measurement noise are approximately equal. For example, the current noise and the voltage noise acting on the total input capacitance are approximately equal. However, this represents a trade-off in the first stage amplifier design for the known input impedance, and the two conventional types of measurement apparatus ultimately reach limitations inherent to their mechanical designs. For the patch pipette, the limitation is the pipette itself. For the Teflon cup, the limitation is the area of the membrane. As a result, in the twenty or so years that patch pipette and the related artificial bilayer measurements have been performed, there have been only marginal sensitivity and bandwidth improvements, and these have been almost entirely due to advances in electronics technology.

Based on the above, there exists a need for a system that will make a substantial improvement in ion channel recordings. Such a system must provide the required electrical properties to improve upon the sensitivity and bandwidth obtained by the well-optimized existing technology, and must also be no more difficult to use, and no more expensive than current technology.

SUMMARY OF THE INVENTION

The present invention is directed to an electrolytic sensing apparatus or system and method of sensing a time varying ionic current. In accordance with the invention, the apparatus includes first and second fluid volumes or chambers that are filled with an electrolyte and separated by a substrate having one or more orifices therein. An analyte(s) of interest is introduced into one or both chambers. The apparatus further includes a first electrode positioned in the first chamber or electrolyte bath, and a second electrode positioned in the second chamber or sensing volume. Establishing a potential difference between the first and second electrodes produces an electric field. The electric field causes an ionic current to flow through the one or more orifices connecting the fluid volumes. A high sensitivity electrical readout circuit is connected across each orifice and coupled to the first and second chambers using either predominantly resistive (e.g. faradaic) or capacitive electrodes connected to the input of a first stage amplifier. This amplifier is in turn connected to subsequent stages of amplification.

Preferably, the orifices are covered by one or more membranes that allow insertion of one or more ion channels. The electrical resistance across an orifice with a membrane attached is in the order of 1 gigaohm (GΩ), and preferably higher in order to minimize the electrical current that flows in parallel with the ion channel current. Alternatively, the apparatus is operated without the orifice being sealed by a membrane, for example to detect the change in current due to particles passing through the orifice. However, in this case the invention is preferably utilized at higher frequencies. For example, an orifice with a diameter of 20 nanometers (nm) (approximately the present state of the art in making nanoscale orifices in glass and silicon) has conductivity when filled with 1 molar (M) potassium chloride (KCl) solution in the order of 10 megaohms (MΩ). In this case, the invention is preferably utilized to measure signals above 1 kilohertz (kHz). For a larger orifice, or for multiple orifices, the frequency at which the apparatus operates in an optimal manner becomes higher in linear proportion to the change in total conductivity.

The membrane can be formed over the orifice by the method of painting, by vesicle fusion or other method known in the art. The form of the membrane depends on the hydrophobicity of the substrate surface. The membrane can be formed from a lipid bilayer, or any material that has similar properties, for example polydimethysiloxane (PDMS). In addition, the membrane can be extracted from a living cell in the manner used for patch clamping.

In contrast to the prior art systems discussed above, the system built in accordance with the present invention has a total capacitance at an amplifier input, including the amplifier itself, of 2-10 pF. This dramatic reduction in the capacitance provides a reduction in the system's internal noise, or current noise, thereby providing a significant increase in sensitivity. This improvement can be utilized whether a system orifice is open, as when a resistive pulse technique is utilized to count and size particles, or whether a membrane and ion channel are present across the orifice. Further, the reduction in internal noise enables measurements to be conducted at bandwidths well beyond the range of prior art systems. Because of its improved sensitivity, the apparatus allows use of a reduced ionic current. This enables implementation with the use of a lower bias voltage or the use of lower concentration electrolytes. Advantageously, the system of the present invention is no more difficult to use, and no more expensive than prior art technology.

The present invention provides higher measurement sensitivity and bandwidth by combining three specific approaches to minimize the capacitance connected to the first stage amplifier input. First, the apparatus includes an orifice having a lateral dimension that is less than 10 μm, and less than 50 nm in the case that no membrane seals the orifice. Secondly, to take advantage of the very small orifice capacitance, the capacitance connecting the first and second fluid volumes that appears across the substrate containing the one or more orifices is less than 1 pF and preferably less than 0.25 pF. This is achieved by minimizing the area of the substrate that is exposed to the fluid and making the substrate sufficiently thick. Thirdly, the measurement electrodes and first stage amplifier are integrated within 5 cm of the nanoscale orifice, and novel circuit designs and packaging provide very high sensitivity for very high input impedance within a small overall volume.

With this preferred arrangement, the ionic current flowing through a small fluid orifice or ion channel is measured with a sensitivity and bandwidth that significantly exceeds prior methods. The fundamental parameter of interest, is the time variation of the ionic current. However, other physical variables such as leakage current of the membrane or another steady state, or quasi steady state property could, in some cases, be a parameter of interest. In the preferred embodiment of an ion channel spanning a membrane, the ion channels can be of their natural form or be engineered or otherwise modified as desired for specific properties. A particular application of the invention is to measure discrete conductivity states in ion channels. These states change stochastically in the presence of analytes in a manner that allows separate determination of concentration and species. Another application of the invention is to measure channel current when conductivity is simply determined by a blocking effect produced by the presence of an analyte in the orifice, as in the conventional Coulter counter.

Additional objects, features and advantages of the present invention will become more readily apparent from the following detailed description of preferred embodiments when taken in conjunction with the drawings, wherein like reference numerals refer to corresponding parts in the several views.

DETAILED DESCRIPTION OF THE PREFERRED EMBODIMENT

Figure 3:
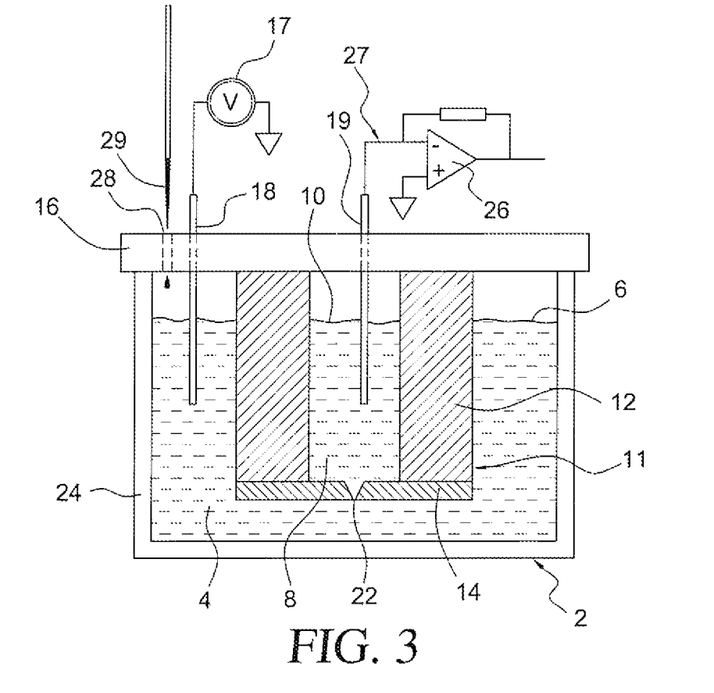
FIG. 3 shows across-sectional view of an apparatus constructed in accordance with the present invention.

With initial reference to FIG. 3, an electrolytic sensing apparatus or system constructed in accordance with the invention is generally indicated at 2. Sensing system 2 includes a first fluid chamber or electrolyte bath 4 within which is provided a first electrolyte 6, and a second fluid chamber or sensing volume 8 provided with a second electrolyte 10. Sensing volume 8 is separated from electrolyte bath 4 by a barrier structure 11 comprised of a thick wall barrier 12 and a substrate 14 that are joined with a seal (not shown) having an electrical resistance of at least 1 GΩ, and preferably higher. Alternatively, structure 11 can be formed as a single unit, such as by casting or molding. In the embodiment shown, structure 11 is in the form of a tube. However, it should be understood that: structure 11 could be various geometric shapes.

A mounting substrate 16 extends across the top of electrolyte bath 4 and sensing volume 8. Measurement electrodes 18 and 19 extend through mounting substrate 16 and into electrolyte bath 4 and sensing volume 8, respectively. In accordance with the invention, wall 12 is made of a very low conductivity material and is preferably at least 0.2 mm in thickness, with an internal diameter of 1 mm. Such a wall thickness and diameter result in a capacitance per mm of immersed length of wall 14 of 0.1 pF per mm as given by the formula $C=2\pi\in/\ln(d_{outer}/d_{inner})$. More preferably, the thickness of wall 12 is at least 0.4 mm, resulting in a capacitance per unit length of 0.06 pF per mm.

For a structure 11 having an internal diameter of 1 mm, the area of electrolyte 10 facing electrolyte bath 4 across substrate 14 is 0.78 mm². Substrate 14 is preferably at least 25 μm in thickness, providing a capacitance of 1 pF in accordance with the formula $C=\in A/t$, where t is the thickness of substrate 14. The average thickness of substrate 14 is more preferably at least 50 μM, limiting the capacitance coupling the two electrolyte volumes 4 and 8 to 0.5 pF or less. In these calculations, a circular cross section has been assumed for convenience, but it should be understood that square cross-sections or any other geometry may be utilized. Overall, the capacitance that couples the inner electrolyte volume 8 to the outer electrolyte volume 4 across structure 11 is preferably less than 2 pF and more preferably less than 0.25 pF.

Substrate 14 contains an orifice 22. Orifice 22 is preferably less than 10 μm when utilized with a membrane, and less than 50 nm when utilized without a membrane. In both cases, the performance is improved with decreased orifice area. However, below a diameter of 3 μm for the case of a membrane seal, the capacitance across the membrane is small compared to other capacitances at the input and no further significant improvement is achieved. For the case of no membrane, the orifice diameter should be as small as possible, preferably less than 20 mm and more preferably less than 10 nm. This nanoscale-type orifice 22 can be constructed by the track etch method, by conventional silicon processing or by the method of sealing a wire in glass and removing it. Orifice 22 is shown conical in order to minimize the electrical resistance of fluid (electrolyte) in series with the constriction of orifice 22. However, it is not essential that orifice 22 be conical, and a cylinder or any other shape could be used provided the electrical resistance in series with an ion channel positioned over orifice 22 is less than approximately 10 times the ion channel resistance.

Substrate 14 is made of a plastic such as polyimide, very low conductivity silicon, glass, quartz, sapphire or any equivalent material. The principal requirements for substrate 14 are that it has a low electrical conductivity, low dielectric loss tangent, and, preferably, be sufficiently flat to support a membrane with a high resistance electrical seal. Substrate 14 and separation wall 12 are preferably formed from the same material. In the case that a wafer substrate such as silicon is used, it is possible to substantially reduce the area of substrate 14 that is exposed to electrolyte by conventional semiconductor processing methods. If the area is reduced, substrate 14 can be much thinner and still provide an adequately small capacitance. For ease of fabrication of orifice 22 by conventional photolithography methods, the substrate area exposed to electrolyte is chosen so that substrate 14 preferably has a thickness of less than 1 μm.

Thick wall 12 and an outer wall 24 of electrolyte bath 4 are connected together by mounting substrate 16. As previously mentioned, measurement electrodes 18 and 19 are connected to mounting substrate 16 and make contact with electrolyte 6, 10 in electrolyte bath 4 and sensing volume 8, respectively. The electrodes 18 and 19 can be of either a conventional non-polarizable type, such as silver/silver chloride (Ag/AgCl) or of a non-reactive material such as platinum (Pt) if an entirely AC method is used.

A first stage amplifier 26 is mounted directly onto mounting substrate 16 in order to minimize the length of a wire 27 connecting amplifier 26 to electrode 19. Preferably, wire 27 is no longer than 5 cm and more preferably less than 2 cm. Additionally, the circuits associated with amplifier 26 include guarding and grounding circuits (not shown) to further minimize stray capacitance, as well as an associated feedback control loop (not separately labeled). One or more holes 28 are made in mounting substrate 16 to allow input and output of electrolyte 6, 10 and an analyte 29.

A voltage to drive the ionic current between electrodes 18 and 19 may be applied as shown in FIG. 3. Preferably, a voltage source 17 is connected to bath electrode 18 and referenced to the system electrical ground. The readout amplifier 26 is connected in a current to voltage converter mode with its positive input connected to ground. Alternatively, it may be more convenient to connect voltage source 17 to the positive input terminal of amplifier 26. In addition, a separate electrode (not shown) connected to a high impedance buffer may be immersed in bath 4. The output of this reference; electrode may be separately recorded in order to provide a more direct measure of the potential of bath 4.

Figure 4:
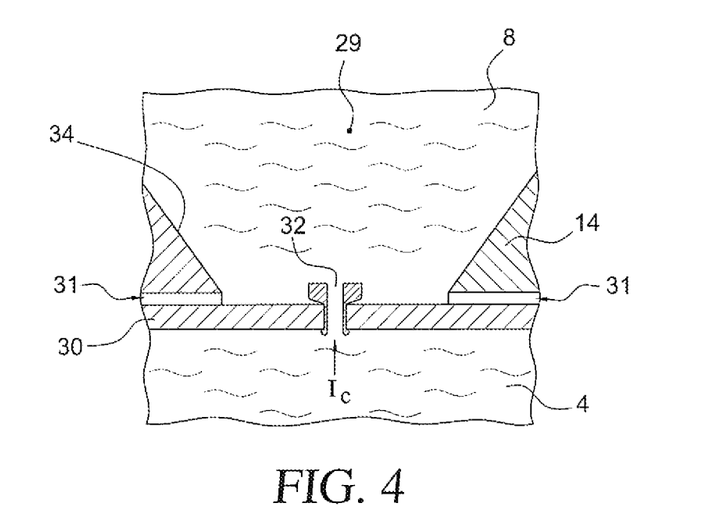
FIG. 4 shows a partial cross-sectional view of the orifice of FIG. 3, including a lipid membrane.

Electrolytes 6 and 10 are typically conventional biocompatible solutions such as 0.1 M KCl, although for non-biological applications, a variety of conducting fluids or solutions could be used. In use, a voltage source 17 is utilized to apply an electrical potential between electrodes 18 and 19 to drive an electrical current between them, and through nanometer sized orifice 22. The driving voltage can be DC as in the conventional practice used in measuring ion channel currents or an AC drive can be used and the resulting current demodulated by methods known to those skilled in the art. The fundamental parameter of interest is a time-varying ionic current $I_c$ that passes through orifice 22 from bath 4 to sensing chamber 8, in response to a target analyte 29, as shown in FIG. 4.

As shown, substrate 14 separates electrolyte bath 4 and sensing volume 8. In some cases the open orifice 22 can be used as is without further modification, in order to detect the presence of objects near the orifice by their effect on the electrical current passing through the orifice. However, orifice 22 is preferably spanned by a lipid bilayer or bilipid membrane 30 (as depicted in FIG. 4), an equivalent material such as PDMS, a liquid film or even a solid material that allows ion channel insertion in some manner. The membrane can be formed over the orifice by the method of painting, by vesicle fusion or by another known method in the art. The form of the membrane depends on the hydrophobicity of the substrate surface. Preferably, membrane 30 produces an electrical resistance (seal resistance) between electrolyte bath 4 and electrolyte 10 in the order of 10 GΩ. In particular it is found that lipid membranes on glass produce a seal 10 GΩ or higher.

In the case of membrane 30, the configuration of the bilayer depends on the surface properties of substrate 14. For a hydrophilic substrate such as glass, membrane 30 forms as a single bilayer over the entire surface of substrate 14 upon a small cushion of water 31, as shown in FIGS. 4 and 6-8. However, if substrate 14 is made from a hydrophobic material such as Teflon, or its outer surface is coated with a hydrophobic material, the bilayer will form only in the region over orifice 22.

Most preferably, membrane 30 has an ion channel 32 inserted in it that spans membrane 30 individually or in some combination with other ion channels. In the most preferred case, ion channel 32 spans the region of membrane 30 directly over orifice 22. When membrane 30 spans substrate 14, an ion channel 32 having a physical structure protruding from membrane 30 may be trapped by an inside wall portion 34 of orifice 22, as shown in FIG. 4, thus preventing ion channel 32 from diffusing away from orifice 22. This is achieved by inserting ion channel 32 from sensing volume 8 via orifice 22. However, results show that it is not essential that ion channel 32 be located exactly in this specific region and in the case that a bilayer membrane 30 covers the substrate 14, channel currents can be measured from ion channels 32 that are in regions of membrane 30 that are nearby orifice 22, such as occurs when an ion channel 32 has inserted into or migrated to a part of membrane 30 directly adjacent to (i.e. over) substrate 14.

Figure 5:
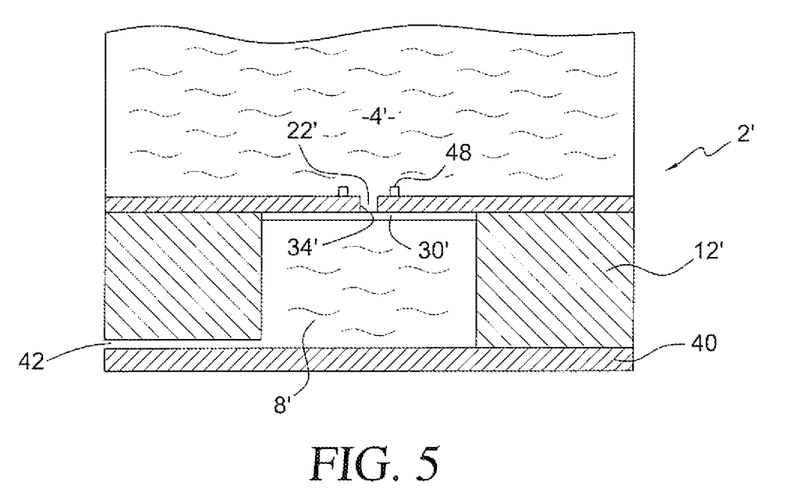
FIG. 5 shows a cross-sectional view of an alternative embodiment of the apparatus of the present invention.

Another possible configuration is for membrane 30 to be located on the inside of substrate 14, i.e. within the sensing volume 8, rather than electrolyte bath 4. This embodiment relates to an apparatus 2' shown in FIG. 5, which is a structure especially applicable to producing an array of sensing elements in a solid material such as a silicon wafer. It uses the bulk of the solid material (e.g. Si) to provide a thick wall barrier 12' with a base 40, such as PDMS, on the bottom of barrier 12' to create a small fill line 42 to allow access to a sensing volume 8'. An ion channel (not shown in FIG. 5 but corresponding to ion channel 32 of the first embodiment) is inserted into a membrane 30' from a bath side 4' via a nanopore or orifice 22' in a barrier 12'. If desired, an electrophoretic or conducting ring 48 is made on barrier 12' around the orifice 22' region, and is raised to a desired potential in order to provide an electrostatic force to aid in channel addressing. One benefit of the membrane configuration in FIG. 5 is that, like in FIG. 4, ion channels 32 having structure protruding from membrane 30' become trapped within orifice 22' by an inside wall 34' of the orifice 22', thus preventing ion channels 32 from diffusing away. A second benefit is that a minimal area of membrane 30' is exposed to any analyte introduced to the system via bath volume 4', thus minimizing potential chemical stressing of membrane 30' by the analyte. Thirdly, in the case of a membrane 30' that is inherently soluble such as a lipid, the smaller volume of sensing volume 8' limits the total lipid dissolution into electrolyte.

Figure 6:
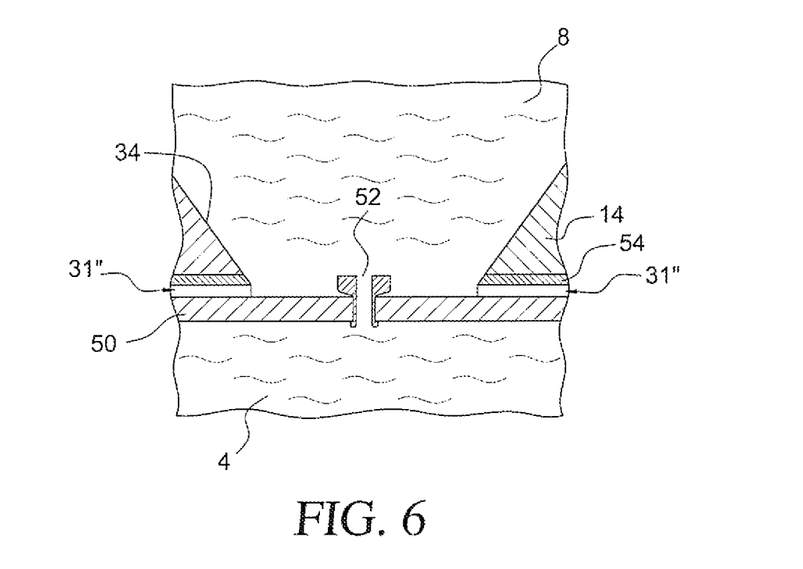
FIG. 6 shows a partial cross-sectional view of the orifice of FIG. 3, including a cell membrane.

The case in which a membrane is extracted from a cell approximates the configuration shown in FIG. 6. In this case, substrate 14 is pressed against a cell (not fully shown), and a membrane 50 is the cell membrane itself, thus at least one cellular ion channel 52 is already present in membrane 50. In this case, substrate 14 is not connected to outer structure 24 of electrolyte bath 4, but rather the apparatus structure 11 and mounting substrate 16 with its associated electronics are free to move within electrolyte bath 4 in order to be placed against cells as desired. To aid in adhering membrane 50, the surface of substrate 14 can optionally be coated with a material 54 such as polylysine or fibronectin, as shown in FIG. 6, though even with such an adhesive layer it is believed that a water layer 31" is still present. In addition, suction can be applied to a sensing volume 8 as in the approach of patch clamping a cell. The higher sensitivity provided by the present invention allows screening of cellular ion channels, such as ion channel 52, that have a conductance too small to be measured by prior technology.

One advantage of the present system design is that the total capacitance at the amplifier input is reduced to 10 pF and more preferably to 6 pF, and most preferably to 2 pF. This total capacitance is the sum of the capacitance across a membrane if present, the capacitance across wall 12 and substrate 14, the capacitance of wire 27 connecting sensing electrode 19 to amplifier 26 to the effective circuit ground, and the capacitance of the transistors and other circuit elements (not shown) including stray capacitances in the amplifier circuit.

Another advantage stemming from the nanoscale orifice of the present invention is that, as the orifice size is reduced, the membrane becomes much more robust mechanically and electrically. The increased electrical robustness is associated with an effective increase in the measurement sensitivity for ion channels that can tolerate applied voltages greater than the conventional limit in the order of 150 millivolts (mV). Generally, the increased voltage induces a channel current that increases in direct proportion, providing a linear increase in the measured signal to noise ratio.

Figure 7:
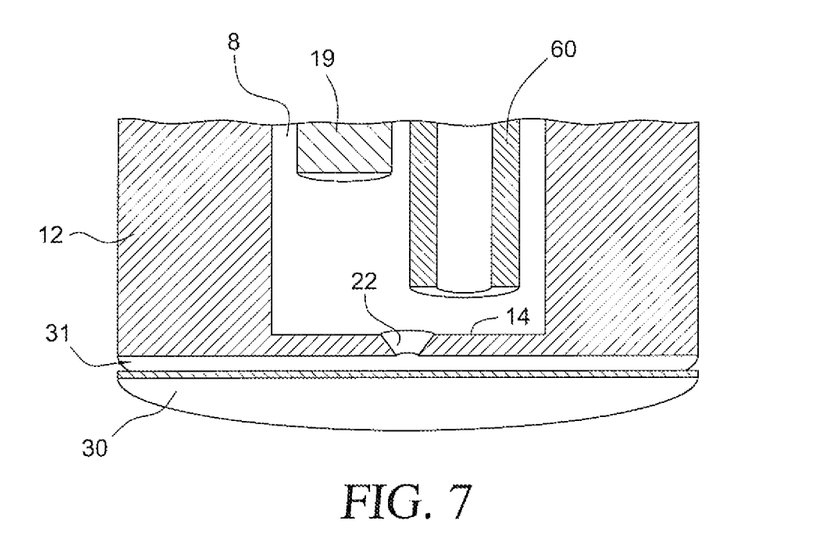
FIG. 7 shows a partial cross-sectional view of the sensing volume of FIG. 3 and a capillary instrument.
Figure 8:
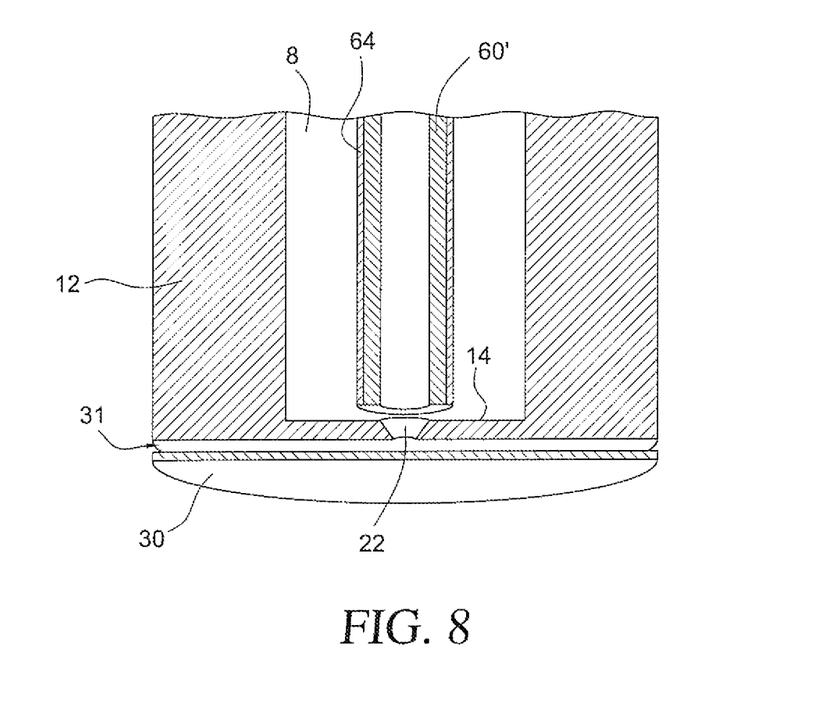
FIG. 8 shows a partial cross-section view of an alternative embodiment of FIG. 7, wherein the capillary instrument is an electrode.

One significant issue in making an orifice very small is the time needed for an ion channel to insert. Scaling from a 100 μm diameter orifice to one that is 1 μm increases the time needed for an ion channel to insert by a factor in the order of 10,000. For a membrane substantially smaller than used in standard patch pipetting, the insertion time could be prohibitively long. For example, for a 25 nm diameter membrane, the insertion time would be 16,000,000 times longer than a conventional artificial membrane experiment. One solution to reduce the insertion time is to deliver the ion channel as close as possible to the orifice region. A way to do this that takes particular advantage of the sensing system configuration of FIG. 3 is shown in FIG. 7. A small capillary 60 is inserted within sensing volume 8 for the purpose of injecting an ion channel or analyte to be tested into the immediate vicinity of orifice 22. The relatively small volume of sensing volume 8 acts as a natural guide to align capillary 60 with orifice 22. In a further embodiment illustrated in FIG. 8, a capillary 60' is coated in a conductor 64, and is used as an electrode such that a separate electrode 19 is not needed. Additionally, electrophoresis or electro osmosis can also be employed to increase the speed of delivering an ion channel to an orifice. Once the ion channel is in the vicinity of the orifice, the confined geometry increases the electric fields, thereby increasing these driving forces.

Figure 9:
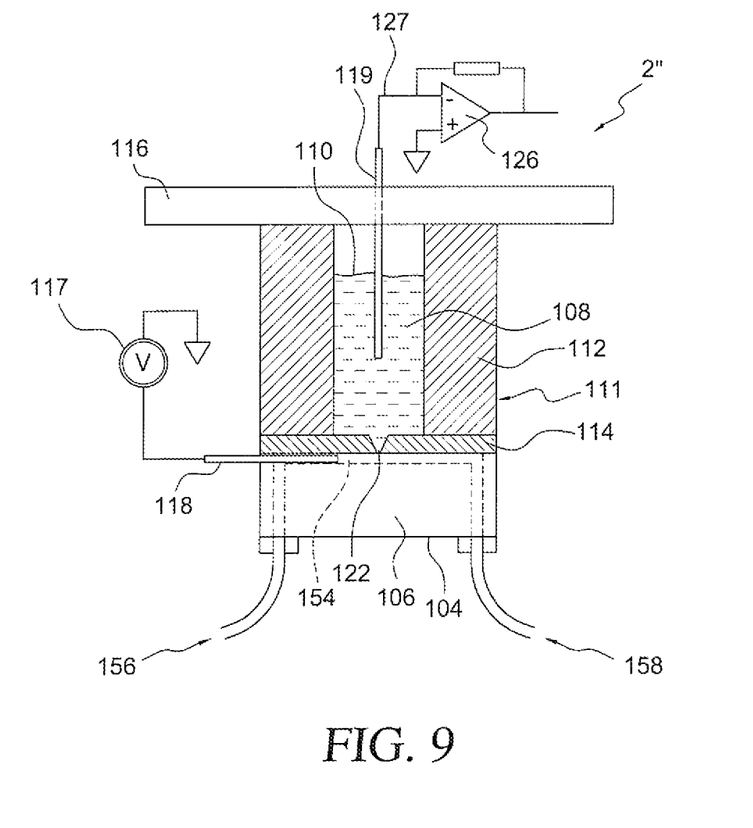
FIG. 9 is a continuous sampling embodiment of the apparatus of the present invention.

A method of utilizing a continuous sampling embodiment 2" of the present invention will now be discussed with reference to FIG. 9. System 2" includes an electrolyte bath or fluid delivery element 104 and an electrolyte bath 108 provided with an electrolyte 110. Fluid delivery element 104 is separated from electrolyte bath 108 by a structure 111 comprised of a thick wall barrier 112 and a substrate 114. Additionally, a mounting substrate 116 extends across the top of electrolyte bath 108. Measurement electrodes 118 and 119 extend into fluid delivery element 104 and electrolyte bath 108, respectively. Substrate 114 contains an orifice 122. Recording electronics 126 are connected to electrode 119 by a conductor wire 127. A voltage source 117 is connected to bath electrode 118 and referenced to the system electrical ground. Delivery element 104 is attached to substrate 114 in a fluid-tight manner and contains a fluid-filled channel 154, which passes over orifice 122 for the purpose of delivering fluid samples of interest to the area of orifice 122. Fluids are input into delivery element 104 at an access port 156, and removed at all exit port 158. Measurement electrode 118 is mounted within channel 154 as shown, or within a fluid volume that is connected to channel 154 by a low electrical impedance. Channel 154 can be any convenient size as determined by the sample input and output requirements. In some cases, the cross-section area of channel 154 and/or its length are made as small as possible to minimize the amount of analyte that must be collected. In these cases, the cross-section of channel 154 is preferably less than 1 mm$^2$ and most preferably channel 154 is made within delivery element 104 by microfluidic technology and has a cross-section in the area of orifice 122 in the order of 10 μm wide×10 μm high, and has a length in the order of 1 cm.

The invention allows for key advances over existing technologies by reducing the capacitance in parallel with an ion channel via use of a very small (nanoscale) membrane area (i.e. across the orifice), use of a relatively thick wall barrier structure compared to the "patch pipettes" used in most conventional measurements, and the highly integrated design that further minimizes conductor length. Further, the very small orifice allows the use of larger applied voltages, producing larger channel currents. Additionally, in the prior art, electrolyte conductivity is traditionally set at the high end of acceptable levels in order to maximize the ionic current. In some cases, it would be desirable to reduce the electrolyte concentration, or measure properties over a range of concentrations. However, this is not typically done in the prior art due to signal to noise ratio (SNR) considerations. The superior sensitivity of the present system allows the use of a reduced ion current. This enables implementation with the use of a lower bias voltage or the use of lower concentration electrolytes. For example, a five times improvement in system sensitivity enables the bias voltage to be reduced from 100 mV to 20 mV, or the electrolyte concentration to be reduced from 1 M to 0.2M.

Figure 10:
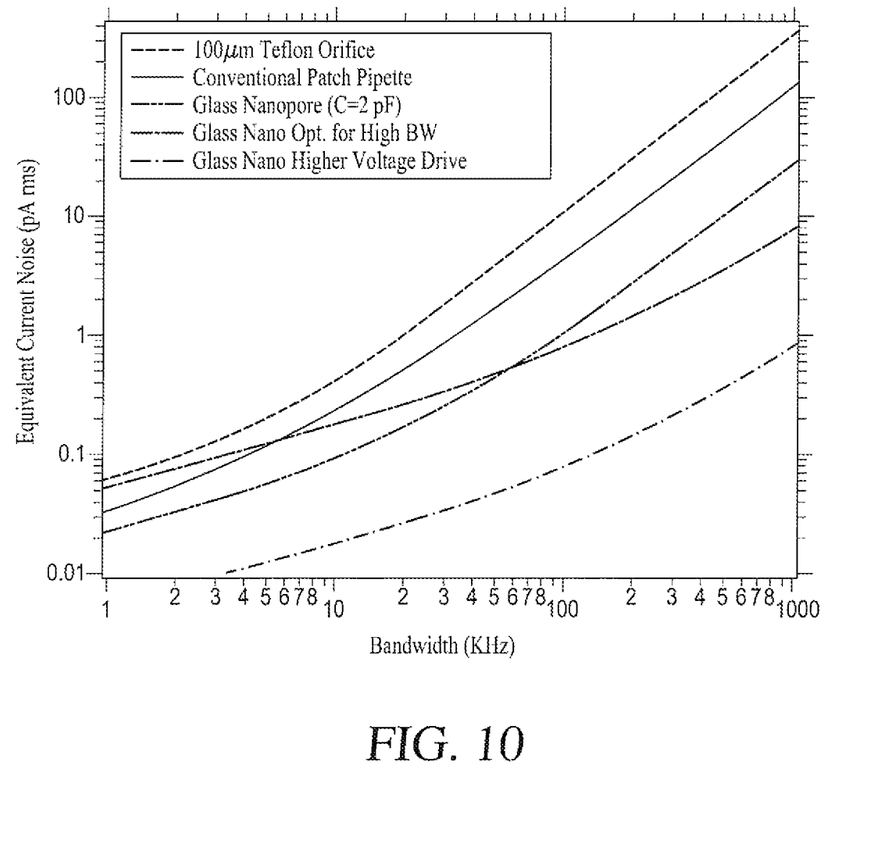
FIG. 10 is a table comparing the sensitivity of the present apparatus with that of conventional patch clamp and artificial membrane systems.

FIG. 10 compares the improvements in sensitivity and bandwidth with conventional Teflon orifice (artificial membrane) and patch pipette systems. Also shown is the effect of increasing the applied bias voltage by a factor of 10 on the equivalent sensitivity at the amplifier input or recording electronics.

As depicted in FIG. 10, at presently used measurement frequencies of 2-10 kHz, there is an increase in sensitivity of a factor of 2 to 4, and 20 to 40 if a ten times higher voltage is used. In addition, the system offers a five to ten times increase in measurement bandwidth over the prior art at standard sensitivity levels, depending on whether the first stage amplifier is optimized for performance at higher frequencies. This increase in bandwidth has immediate application in detecting events that produce very rapid changes in electrical current, such as DNA passing through a channel. To date, such rapid changes cannot be measured directly.

Although described with reference to preferred embodiments of the invention, it should be readily understood that various changes and/or modifications can be made to the invention without departing from the spirit thereof. For instance, although the various embodiments shown in is the figures depict single ion channel systems, it should be understood that the present invention may also be utilized with an array of sensing elements. In general, the invention is only intended to be limited by the scope of the following claims.

We claim:

1. An apparatus for sensing a time varying ionic current in an electrolytic system comprising:
    a first fluid chamber defining an electrolyte bath containing a first electrolytic fluid;
    a second fluid chamber defining a sensing volume containing a second electrolytic fluid;
    a barrier structure including a wall portion, having a thickness of at least 0.2 mm, and a substrate with an orifice located therein, said barrier structure separating the first and second fluid chambers, the second fluid chamber being in communication with said first fluid chamber via the orifice, a voltage source for establishing a potential difference across the barrier structure for the purpose of driving an ionic current through the orifice;
    an electrode positioned to sense the time varying ionic current passing through the orifice from the first fluid chamber to the second fluid chamber and thus create an ionic current signal; and
    an amplifier connected to the electrode by wiring and located proximal the barrier structure, said amplifier amplifying the ionic current signal, wherein the total capacitance at the amplifier input is less than 10 pF during operation of the apparatus.

2. The apparatus of claim 1, wherein the total capacitance coupling the first fluid chamber and the second fluid chamber is less than 2 pF.

3. The apparatus of claim 1, wherein the total capacitance coupling the first fluid chamber and the second fluid chamber is less than 0.25 pF.

4. The apparatus of claim 1, wherein the wiring is less than 5 cm in length.

5. The apparatus of claim 1, wherein the wall portion has a thickness of at least 0.4 mm.

6. The apparatus of claim 1, wherein the barrier structure is tubular and sealed at one end.

7. The apparatus of claim 1, wherein the barrier structure is a silicon wafer.

8. The apparatus of claim 1, further comprising a membrane sealing the orifice.

9. The apparatus of claim 8, wherein the diameter of the orifice is less than 10 µm.

10. The apparatus of claim 1, wherein the diameter of the orifice is less than 50 nm.

11. The apparatus of claim 8, further comprising an ion channel spanning the membrane.

12. The apparatus of claim 8, wherein the membrane is a cell membrane.

13. The apparatus of claim 8, wherein the membrane seals the orifice on a sensing volume side of the substrate.

14. The apparatus of claim 8, further comprising a coating on the substrate adapted to aid in the sealing of the membrane over the orifice.

15. The apparatus of claim 11, wherein the ion channel is trapped within the orifice by an inside wall of the substrate.

16. The apparatus of claim 1, further comprising a microfluidic channel adapted to transport an analyte to the orifice.

17. The apparatus of claim 1, further comprising a capillary adapted to transport an analyte to the orifice.

18. The apparatus of claim 17, wherein the capillary supports the sensing electrode.

19. An apparatus for sensing a time varying ionic current in an electrolytic system comprising:
a first fluid chamber defining an electrolyte bath containing a first electrolytic fluid;
a second fluid chamber defining a sensing volume containing a second electrolytic fluid;
a barrier structure including a wall portion and a substrate with an orifice located therein, said barrier structure separating the first and second fluid chambers, the second fluid chamber being in communication with said first fluid chamber via the orifice, a voltage source for establishing a potential difference across the barrier structure for the purpose of driving an ionic current through the orifice, wherein the substrate has a thickness of at least 25 µm and an area of the substrate portion that is exposed to the fluid is less than 1 mm$^2$;
an electrode positioned to sense the time varying ionic current passing through the orifice from the first fluid chamber to the second fluid chamber and thus create an ionic current signal; and
an amplifier connected to the electrode by wiring and located proximal the barrier structure, said amplifier amplifying the ionic current signal, wherein the total capacitance at the amplifier input is less than 10 pF during operation of the apparatus.

20. The apparatus of claim 19, wherein the wall portion has a thickness of at least 0.2 mm.

21. An apparatus for sensing a time varying ionic current in an electrolytic system comprising:
a first fluid chamber defining an electrolyte bath containing a first electrolytic fluid;
a second fluid chamber defining a sensing volume containing a second electrolytic fluid;
a barrier structure including a wall portion and a substrate with an orifice located therein, wherein the substrate has a thickness of less than 1 µm, said barrier structure separating the first and second fluid chambers, the second fluid chamber being in communication with said first fluid chamber via the orifice, a voltage source for establishing a potential difference across the barrier structure for the purpose of driving an ionic current through the orifice;
an electrode positioned to sense the time varying ionic current passing through the orifice from the first fluid chamber to the second fluid chamber and thus create an ionic current signal; and
an amplifier connected to the electrode by wiring and located proximal the barrier structure, said amplifier amplifying the ionic current signal, wherein the total capacitance at the amplifier input is less than 10 pF during operation of the apparatus.

22. In an apparatus including: a first fluid chamber defining an electrolyte bath containing a first electrolytic fluid; a second fluid chamber defining a sensing volume containing a second electrolytic fluid; a barrier structure including a wall portion, having a thickness of at least 0.2 mm, and a substrate with an orifice located therein; a voltage source for establishing a potential difference across the barrier structure for the purpose of driving an ionic current through the orifice; an electrode positioned to sense the time varying ionic current passing through the orifice from the first fluid chamber to the second fluid chamber and thus create an ionic current signal; and an amplifier connected to the electrode by wiring and located proximal the barrier structure, said amplifier amplifying the ionic current signal, a method of sensing a time varying ionic current in an electrolytic system including the first fluid chamber separated from the second fluid chamber by the barrier structure containing the orifice, the second fluid chamber being in communication with the first fluid chamber via the orifice, the method comprising:
placing an analyte in the first fluid chamber;
establishing a potential difference across the barrier structure and driving a time varying ionic current through the orifice; and
sensing the time varying ionic current passing through the orifice from the first fluid chamber to the second fluid chamber, wherein the total capacitance at the amplifier input is less than 10 pF during operation of the apparatus.

23. The method of claim 22, further comprising:
sealing the orifice with a membrane thus suspending a portion of the membrane over the orifice; and
placing an ion channel over the portion of the membrane using the barrier structure as a guide.

24. The method of claim 23, further comprising:
recording the response of the ion channel to the analyte.

* * * * *